(12) United States Patent
Matsumoto et al.

(10) Patent No.: US 8,205,480 B2
(45) Date of Patent: Jun. 26, 2012

(54) MEASURING DEVICE

(75) Inventors: Toru Matsumoto, Tokyo (JP); Hideyuki Sato, Tokyo (JP)

(73) Assignee: NEC Corporation, Tokyo (JP)

( * ) Notice: Subject to any disclaimer, the term of this patent is extended or adjusted under 35 U.S.C. 154(b) by 468 days.

(21) Appl. No.: 12/593,069

(22) PCT Filed: Mar. 19, 2008

(86) PCT No.: PCT/JP2008/000644
§ 371 (c)(1),
(2), (4) Date: Sep. 25, 2009

(87) PCT Pub. No.: WO2008/129801
PCT Pub. Date: Oct. 30, 2008

(65) Prior Publication Data
US 2010/0083735 A1    Apr. 8, 2010

(30) Foreign Application Priority Data

Mar. 29, 2007  (JP) ................. 2007-086682

(51) Int. Cl.
*G01N 1/22* (2006.01)
(52) U.S. Cl. .............. 73/19.12; 73/19.1; 204/431
(58) Field of Classification Search ............ 73/19.1, 73/19.12; 204/412–431
See application file for complete search history.

(56) References Cited

U.S. PATENT DOCUMENTS

| | | | | |
|---|---|---|---|---|
| 4,681,601 A * | 7/1987 | Foster | | 73/19.1 |
| 4,944,178 A * | 7/1990 | Inoue et al. | | 73/19.1 |
| 5,528,923 A * | 6/1996 | Ledez et al. | | 73/19.12 |
| 6,248,224 B1 * | 6/2001 | Kitzelmann | | 204/431 |

FOREIGN PATENT DOCUMENTS

| | | |
|---|---|---|
| JP | 2001-281204 A | 10/2001 |
| JP | 2002-544478 A | 12/2002 |

* cited by examiner

*Primary Examiner* — Hezron E Williams
*Assistant Examiner* — Hoang Nguyen
(74) *Attorney, Agent, or Firm* — Dickstein Shapiro LLP (57) ABSTRACT

The measuring device 1 includes a measurement vessel 13 contained a liquid 12 filled therein, and a sensor 11 provided in the measuring vessel 13 and for detecting components of a gaseous sample dissolved in the liquid 12. The measuring device 1 also includes a bubble-generating unit 14, which is supplied with a gaseous sample and has an aperture 141 for discharging the gaseous sample in form of bubbles into the liquid. The aperture 141 faces the sensor 11 and the bubble-generating unit 14 is disposed to have a predetermined clearance with the sensor 11. A relation of $1/2Y \leqq X \leqq 3/2Y$ is satisfied, where X represents a distance of a clearance between the bubble-generating unit 14 and the sensor 11 and Y represents a diameter of the aperture 141 of the bubble-generating unit 14.

13 Claims, 5 Drawing Sheets

MEASURING DEVICE

TECHNICAL FIELD

The present invention relates to a measuring device.

BACKGROUND ART

Figure 7:
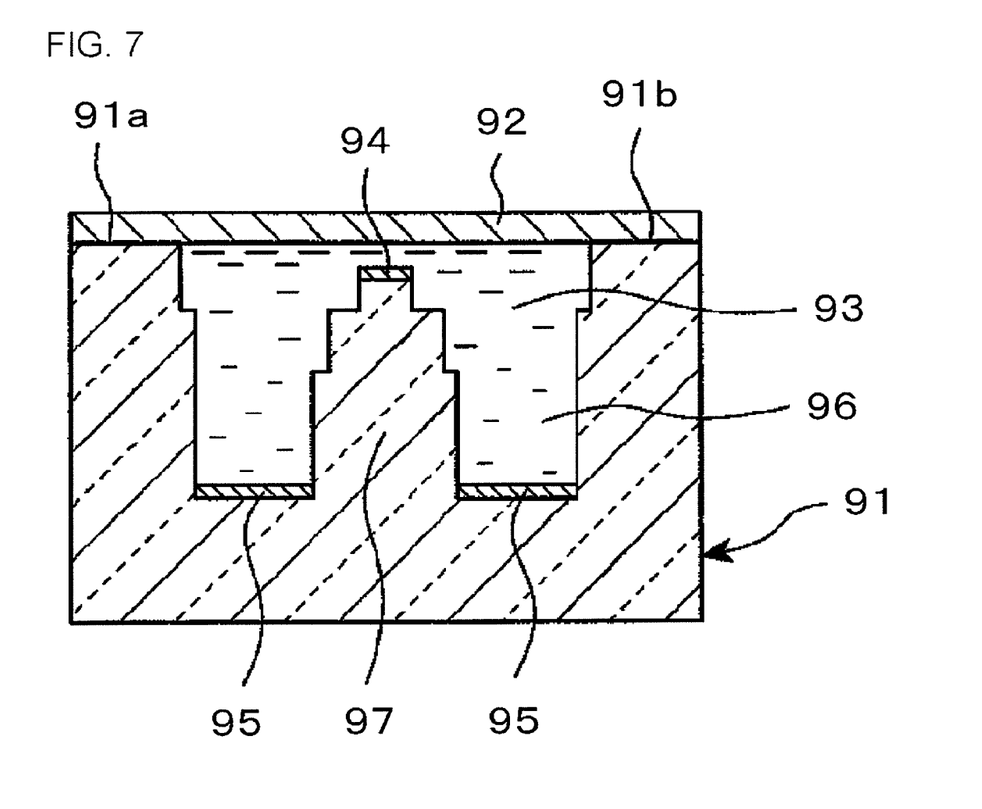
[FIG. 7] It is a diagram, illustrating a conventional measuring device.

Conventionally, a measuring device as shown in FIG. 7 is employed for a measuring device for measuring components in a gaseous sample. Such measuring device is a diaphragm-type sensor, which includes a sensor main frame 91, a gas-liquid separator film 92, an electrolytic solution 93, a detection electrode 94 and counter electrodes 95. The sensor main frame 91 includes a pair of film joint surfaces 91a and 91b, on which a gas-liquid separator film 92 is joined, electrolytic solution-containing trenches 96 provided in a location between film joint surfaces 91a and 91b and a detection electrode pedestal 97 projected from the bottom surface of the electrolytic solution-containing trenches 96. A detection electrode 94 is provided on a surface of a tip of the detection electrode pedestal 97 of the sensor main frame 91, and the counter electrodes 95 are provided on the bottom surface of the electrolytic solution-containing trenches 96.

[Patent Document 1]
Japanese Patent Laid-Open No. 2001-281,204

DISCLOSURE OF THE INVENTION

In recent years, measurements for components of gaseous samples with an enhanced accuracy in shorter time and measurements for components of gaseous samples over multiple cycles are required. In order to more accurately measure components of gaseous samples, it is necessary to ensure dissolving the gaseous sample in a liquid employed in the measuring device (for example, electrolytic solution 93).

However, no disclosure on a configuration for enhancing a dissolution of a gaseous sample is made in the Patent Document 1, and thus it is considered that the measurement for components of gaseous samples with further enhanced accuracy is difficult.

In addition thereto, since no consideration is made on the measurements in shorter time and the measurements over multiple cycles in the Patent Document 1, it is difficult to meet the above-described requirements of the measurements for components of gaseous samples in shorter time and measurements for components of gaseous samples over multiple cycles.

As described above, in order to more accurately measure components of gaseous samples, it is necessary to ensure dissolving the gaseous sample in a liquid filled in a measuring vessel. Consequently, it may be considered to provide a bubble-generating unit for generating bubbles of the gaseous sample in the liquid. It was found from the results of the examinations by the present inventors that the following problems lie in the efforts for providing a bubble-generating unit and achieving the measurements in shorter time and the measurements over multiple cycles. In order to measure the components of the gaseous sample within a shorter duration time, it is required to enhance a response speed of a sensor. When the bubble-generating unit is brought to be closer to the sensor for enhancing a response speed of the sensor, the surface of the sensor is dried by the bubbles, deteriorating the response speed. The dried surface of the sensor, in turn, causes a damage on the sensor during the repeated measurements of the gaseous sample for multiple cycles.

On the other hand, larger distance between the bubble-generating unit and the sensor causes a deterioration of the response speed of the sensor, causing a difficulty in the measurement within a shorter duration time.

According to one aspect of the present invention, there is provided measuring device, comprising: a measuring vessel containing a liquid; a sensor provided in the measuring vessel and for detecting components of a gaseous sample dissolved in the liquid; and a bubble-generating unit being supplied with a gaseous sample and having an aperture for discharging the gaseous sample in form of bubbles into the liquid, wherein the aperture faces the sensor and the bubble-generating unit is disposed to have a predetermined clearance with the sensor, and wherein a relation of $1/2Y \leq X \leq 3/2Y$ is satisfied, where X represents a distance of a clearance between the bubble-generating unit and the sensor and Y represents a diameter of the aperture of the bubble-generating unit.

According to the present invention, a measuring device for gaseous samples can be presented, which allows more accurate measurement of the components in the gaseous sample, also allows the measurement within a shorter duration time, and allows the measurements for over multiple cycles.

BRIEF DESCRIPTION OF THE DRAWINGS

The above and other objects, advantages and features of the present invention will be more apparent from the following description of certain preferred embodiments taken in conjunction with the accompanying drawings.

BEST MODE FOR CARRYING OUT THE INVENTION

Preferable embodiments of the present invention will be described as follows in reference to the annexed figures.

(First Embodiment)

First embodiment of the present invention will be described below. General outline of the measuring device 1 of the present embodiment will be described in reference to FIG. 1.

Figure 1:
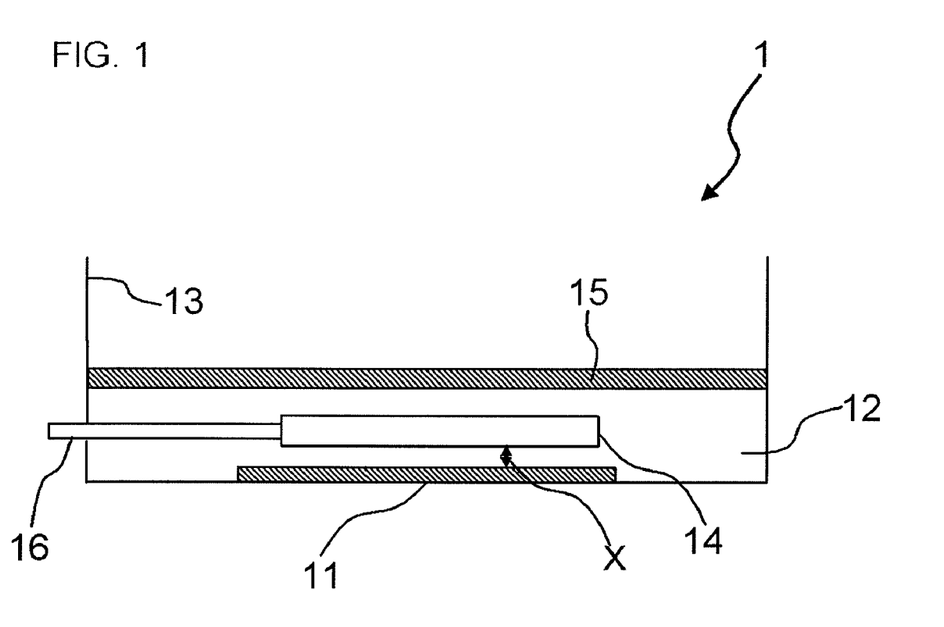
[FIG. 1] It is a schematic diagram, illustrating a measuring device in first embodiment of the present invention.

The measuring device 1 includes a measurement vessel 13 contained a liquid 12 filled therein, and a sensor 11 provided in the measuring vessel 13 and for detecting components of a gaseous sample dissolved in the liquid 12.

Figure 3:
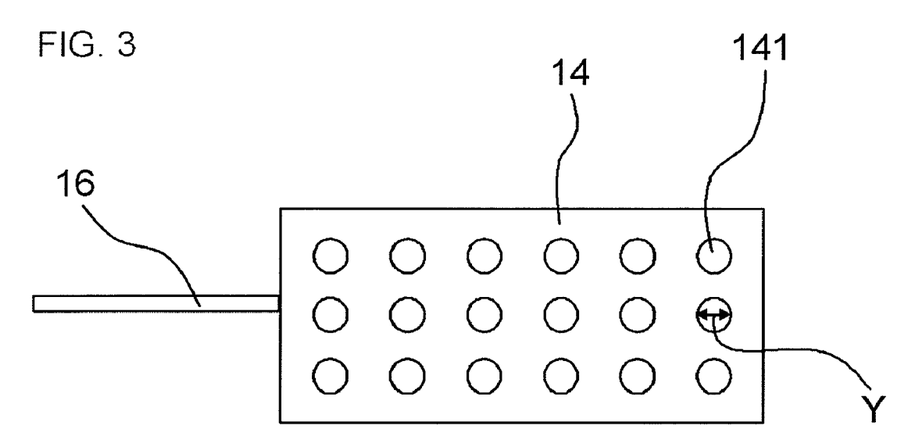
[FIG. 3] It is a plan view, illustrating a bubble-generating unit and a feeding duct of the measuring device.
Figure 4:
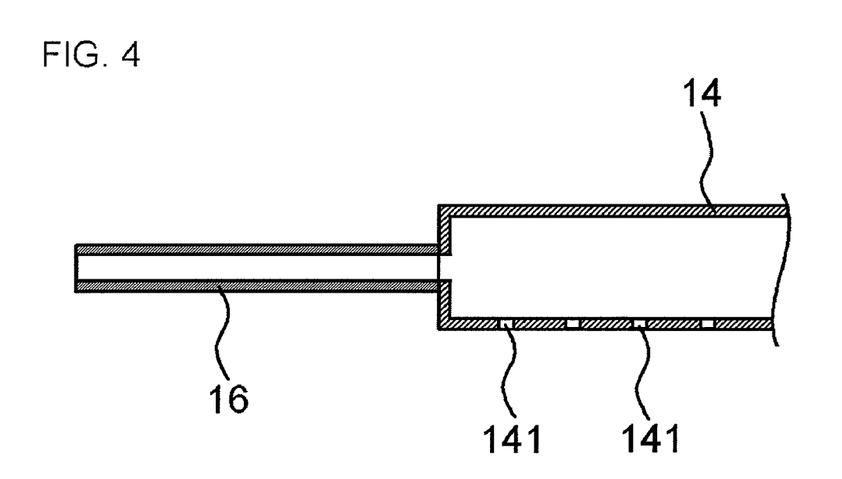
[FIG. 4] It is a cross-sectional view, illustrating the bubble-generating unit and the feeding duct of the measuring device.

The measuring device 1 also includes a bubble-generating unit 14, which is supplied with a gaseous sample and has an aperture 141 for discharging the gaseous sample in form of bubbles into the liquid (see FIG. 3 and FIG. 4). The aperture 141 faces the sensor 11 and the bubble-generating unit 14 is disposed to have a predetermined clearance with the sensor 11. A relation of $1/2Y \leq X \leq 3/2Y$ is satisfied, where X represents a distance of a clearance between the bubble-generating unit 14 and the sensor 11 and Y represents a diameter of the aperture 141 of the bubble-generating unit 14.

Then, the configuration of the measuring device 1 will be fully described. The measuring device 1 is employed for measuring component in a gaseous sample, and for example, for detecting alcohol in a gas containing alcohol. The measuring device 1 includes, in addition to the above-described measuring vessel 13, the liquid 12, the sensor 11, and the bubble-generating unit 14, a gas-liquid separator film 15 and a feeding duct 16. The measuring vessel 13 contains the liquid 12 in the inside thereof, and has the sensor 11 and the bubble-generating unit 14 disposed therein. The upper surface of the measuring vessel 13 is opened. A dimension and a shape of the measuring vessel 13 is not particularly limited, provided that the shape and the size allow installing the sensor 11 and the bubble-generating unit 14 or the like. A plastic may be preferably employed for the measuring vessel 13 to allow facilitating the processing and producing at lower cost.

Figure 2:
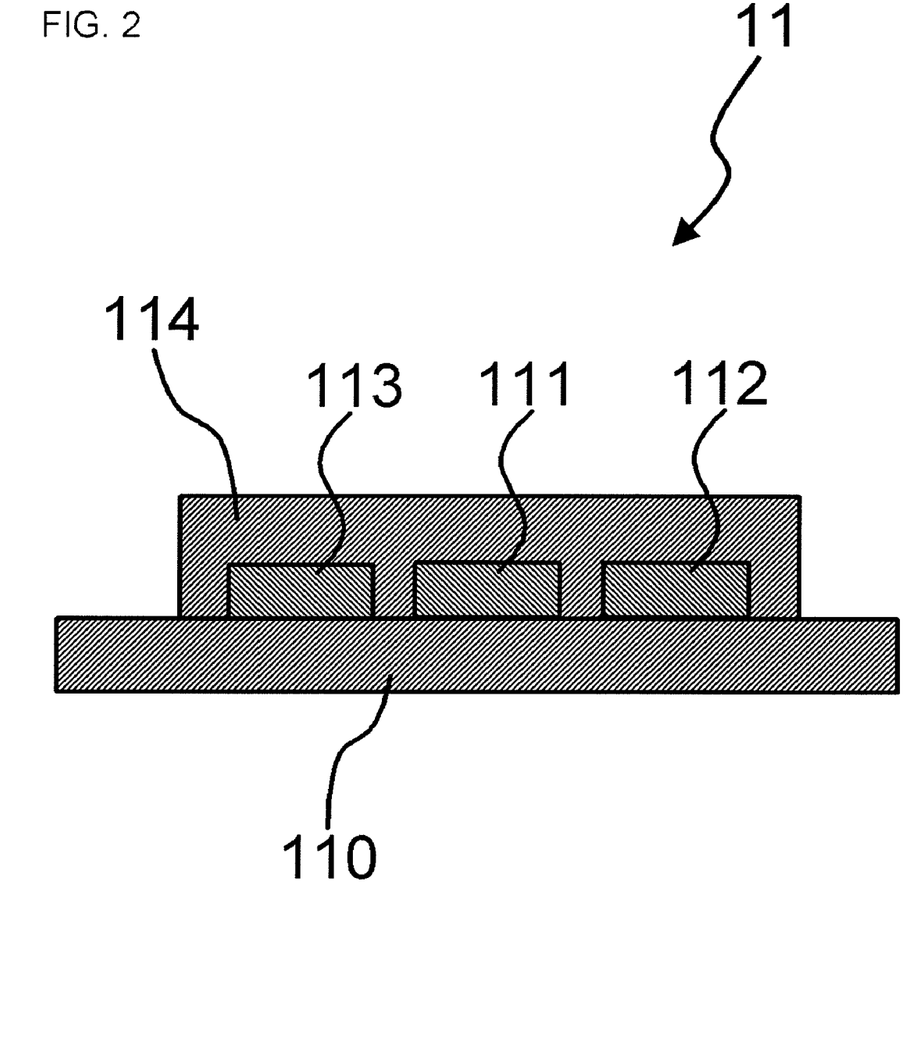
[FIG. 2] It is a cross-sectional view, illustrating a sensor of the measuring device.

The sensor 11 is disposed on a bottom section of the measuring vessel 13. The sensor 11 is a device, which is referred to as a bio sensor, and includes, as shown in FIG. 2, an insulating substrate 110, a detection electrode (working electrode) 111 provided on the insulating substrate 110, a counter electrode 112, and a reference electrode 113. In such configuration, the detection electrode 111 leastwise functions as a working electrode in the electrochemical measurement. Materials such as glass or plastics may be preferably employed for the insulating substrate 110. Protein having a catalyst function of a biological origin is immobilized as a film 114 over the surfaces of the detection electrode 111, the counter electrode 112 and the reference electrode 113. Here, protein may preferably have at least one of an enzyme and an antibody. Oxidase or dehydrase may be preferably employed for an enzyme, and monoclonal antibody or polyclonal antibody may be preferably employed for an antibody.

Materials available for the detection electrode 111, the counter electrode 112, and the reference electrode 113 may be a material, which is capable of detecting an electric current level generated in an enzyme reaction or an antigen-antibody reaction, and more specifically carbon or a precious metal such as platinum and the like may be preferably employed. In particular, a precious metal such as platinum and the like may be preferable for immobilizing an enzyme, and a carbon electrode may be preferable for immobilizing an antibody. The sensor 11 may be an amperometric system, which includes the detection electrode 111, the counter electrode 112 and the reference electrode 113, and is capable of detecting an electric current obtained from the detection electrode 111 that is applied with an electric potential for the reference electrode 113, or may be a potentiometric system, which detects an electric potential difference between the detection electrode 111 and the counter electrode 112. However, the amperometric system is preferable in view of manufacturing the sensor 11 with a reduced cost. In addition to above, other types of sensors except the biosensor, namely a pH sensor, an oxygen sensor, a nitrogen monoxide sensor, a nitrogen dioxide sensor, an ammonia sensor and the like, may also be undoubtedly employed for the sensor 11. Further, multiple sensors may also be selected from the above-described sensors to employ a combination thereof.

The bubble-generating unit 14 is configured to be supplied with a gaseous sample, and to discharge the supplied gaseous sample in a form of bubbles. The bubble-generating unit 14 is disposed to face the sensor 11 with a certain clearance therebetween. As shown in FIG. 3, a plurality of apertures 141 are formed in the bubble-generating unit 14 in the locations facing the sensor 11. FIG. 3 is a plan view of the bubble-generating unit 14 viewed from the side of the bottom surface of the measuring vessel 13. Assume that X represents a distance of a clearance between the bubble-generating unit 14 and the detection electrode 111 of the sensor 11 (more specifically, a clearance between an opening for discharging bubbles in the apertures 141 of the bubble-generating unit 14 (corresponding to an outlet for discharging the gaseous sample to the external of the apertures 141 in the form of bubbles, and not an inlet for introducing gaseous sample within the aperture 141) and the detecting surface of the sensor 11, and Y represents the diameter of the aperture 141 of the bubble-generating unit 14, the following relation is satisfied: $1/2Y \leqq X \leqq 3/2Y$.

In the present embodiment, a surface of the bubble-generating unit 14 facing the detecting surface of the sensor 11 is arranged to be in parallel with the detecting surface of the sensor 11. When the outlet of the aperture 141 is formed to be inclined from the sensor 11, a distance from a central portion of the outlet of the aperture 141 to the sensor 11 may be utilized as X.

Further, X may preferably be equal to or larger than $10/11Y$, and Y may preferably be equal to or smaller than $11/10Y$. In particular, a distance X of a clearance between the bubble-generating unit 14 and the sensor 11 may be more preferably equivalent to the diameter Y of the aperture 141 of the bubble-generating unit 14. The diameter of the aperture 141 of the bubble-generating unit 14 may be preferably equal to or larger than 0.01 mm, and equal to or smaller than 0.1 mm. In particular, the diameter of the aperture 141 may be more preferably equal to or larger than 0.02 mm, and may also be more preferably equal to or smaller than 0.05 mm. Further, the distance X of the clearance of between the bubble-generating unit 14 and the sensor 11 may be preferably within a range of from 0.01 mm to 0.1 mm. In particular, the distance X may be more preferably equal to or larger than 0.025 mm, and may also be more preferably equal to or smaller than 0.05 mm.

In the present embodiment, the bubble-generating unit 14 is configured to have a plurality of apertures 141 formed in the bottom surface of the vessel made of a plastic material, which is rectangular solid-shaped or a cube-shaped. All of the apertures 141 have a substantially constant diameter, and the apertures 141 are arranged on the bottom surface of the vessel with a constant distance. More specifically, the apertures 141 are arranged along the respective sides of the bottom surface of the vessel having the rectangular feature. In such case, clearances X between all the apertures 141 and the sensor 11 (the shortest distances from the apertures 141 to sensor 11) satisfies the above described relation of: $1/2Y \leqq X \leqq 3/2Y$. In addition to above, the configuration of the bubble-generating unit 14 is not limited thereto, and a porous material such as foamed metal, pumice stone and the like may also be employed. In such case, it is sufficient that the relation of $1/2Y \leqq X \leqq 3/2Y$ is satisfied, assuming that X represents the distance of the clearance between the sensor and the aperture nearest to the sensor formed in the bubble-generating unit (the clearance between the opening in the bubble-generating unit discharging bubbles and the sensor) and Y represents the diameter of the aperture of the bubble-generating unit, and it is more preferable that all the apertures satisfies the relation of $1/2Y \leqq X \leqq 3/2Y$. A feeding duct 16 for supplying the gaseous sample such bubble-generating unit 14 is connected to the bubble-generating unit 14. The feeding duct 16 also serves as fixing the bubble-generating unit 14 in the measuring vessel 13. In the present embodiment, the feeding duct 16 is coupled in the substantially middle part of the side surface of the vessel in the bubble-generating unit 14. Materials for the feeding duct 16 is not particularly limited if the material has better corrosion resistance and also has a sufficient mechanical strength for fixing the bubble-generating unit 14, and for example, plastics are preferable. Meanwhile, the gaseous sample is transported through the feeding duct 16 to the bubble-generating unit 14 at a certain pressure, so that bubbles be uniformly generated from all the apertures 141 of the bubble-generating unit 14.

As shown in FIG. 1, the liquid 12 fills an interior of a region comparted by the measuring vessel 13 and the gas-liquid separator film 15. The liquid 12 is a solvent, and contains a pH buffer and an electrolyte. Typical pH buffer includes, for example, a phosphate buffer. Typical electrolyte includes sodium chloride. A very small amount of a alcohol as an organic liquid may be additionally contained, depending on the type of the gaseous sample. This is because such addition may facilitate a measurement of an explosive component that is easy to be dissolved in an organic liquid. Further, the liquid 12 may contain an antiseptic agent.

The gas-liquid separator film 15 is fixed to the measuring vessel 13 to cover the upper surface of the liquid 12. The gaseous sample, which is to be blasted as bubbles from the bubble-generating unit 14, is discharged from the gas-liquid separator film 15.

Tetrafluoroethylene is preferably employed for the gas-liquid separator film 15 for its better handling-ability.

In the measuring device 1 having the above-described configuration, the measurement of the gaseous sample is conducted as follows. First of all, the gas-liquid separator film 15, the sensor 11, the feeding duct 16 and the bubble-generating unit 14 are fixed to the measuring vessel 13. Next, the measuring vessel 13 is filled with the liquid 12 through the feeding duct 16 and the bubble-generating unit 14. This completes the assembly of the measuring device 1. Then, a gaseous sample as a measuring object is supplied to the bubble-generating unit 14 through the feeding duct 16. The gaseous sample is discharged in the form of bubbles within the liquid 12 through the apertures 141 of the bubble-generating unit 14. The gaseous sample in the form of bubbles are quickly dissolved in the liquid 12, and then the measurement of the component of gaseous sample is carried out.

Next, advantageous effects by the present embodiment will be described. Since the measuring device 1 includes the bubble-generating unit 14 having the apertures 141 formed therein for discharging the gaseous sample into the liquid 12, the gaseous sample can be certainly and quickly dissolved in the liquid 12.

In addition, since the distance X of the clearance between the bubble-generating unit 14 and the sensor 11 is selected to be 1/2 or larger, and in particular 10/11 or larger, of the diameter Y of the apertures 141 in the bubble-generating unit 14, unwanted dry of sensor 11 with the bubbles can be prevented. Therefore, a degradation of a response speed of the sensor 11 can be prevented. Further, when multiple cycles of the measurements for the component of the gaseous sample are conducted, a damage on the sensor 11 can be prevented. Further, an interference to the contact of the liquid 12 containing the bubbles dissolved therein with the surface of the sensor 11 by the presence of the bubbles can be prevented, by providing the distance X of the clearance between the bubble-generating unit 14 and the sensor 11 as 1/2 or larger, and in particular 10/11 or larger, of the diameter Y of the apertures 141 in the bubble-generating unit 14. This allows accurate measurement of the component of the gaseous sample.

Since the distance X of the clearance between the bubble-generating unit 14 and the sensor 11 is selected to be 1/2 or larger, and in particular 10/11 or larger, of the diameter Y of the apertures 141 in the bubble-generating unit 14, the distance of the bubble-generating unit 14 and the sensor 11 can be reduced, thereby preventing a degradation of the response speed of the sensor 11. Further, when diameter Y of the aperture 141 of the bubble-generating unit 14 is equivalent to the distance X of the clearance with the sensor 11, drying of the sensor 11 can be more definitely prevented and degradation of the response speed of the sensor 11 can be more definitely prevented.

Since the diameter of the aperture 141 of the bubble-generating unit 14 is selected to be equal to or lower than 0.1 mm, the diameter of the generated bubble can be reduced, thereby enhancing the dissolution rate of the gaseous sample into the liquid 12. Further, the diameter of the aperture 141 of the bubble-generating unit 14 is selected to be equal to or lower than 0.05 mm, so that the gaseous sample can be more definitely dissolved. Moreover, when the diameter of the aperture 141 of the bubble-generating unit 14 is selected to be equal to or lower than 0.01 mm, bubbles of the gaseous sample can be definitely released from the bubble-generating unit 14.

Further, since the gas-liquid separator film 15 is installed above the upper section of the liquid 12 contained in the measuring vessel 13 in the present embodiment, bubbles created in the bubble-generating unit 14 can be promptly discharged to the external. Further, the region comparted by the measuring vessel 13 and the gas-liquid separator film 15 is filled with the liquid 12, so that a leakage of the liquid 12 to the external of the measuring vessel 13 can be avoided. Therefore, the measurement of the component of the gaseous sample can be carried out by inclining the measuring vessel 13, so that improved operationality in the measurement can be achieved.

Further, the measuring vessel 13 is filled with the liquid 12 through the feeding duct 16 and the bubble-generating unit 14 in the present embodiment. Therefore, the inside of the measuring vessel 13 can be filled with the liquid 12 after the measuring device 1 is produced.

(Second Embodiment)

Figure 5:
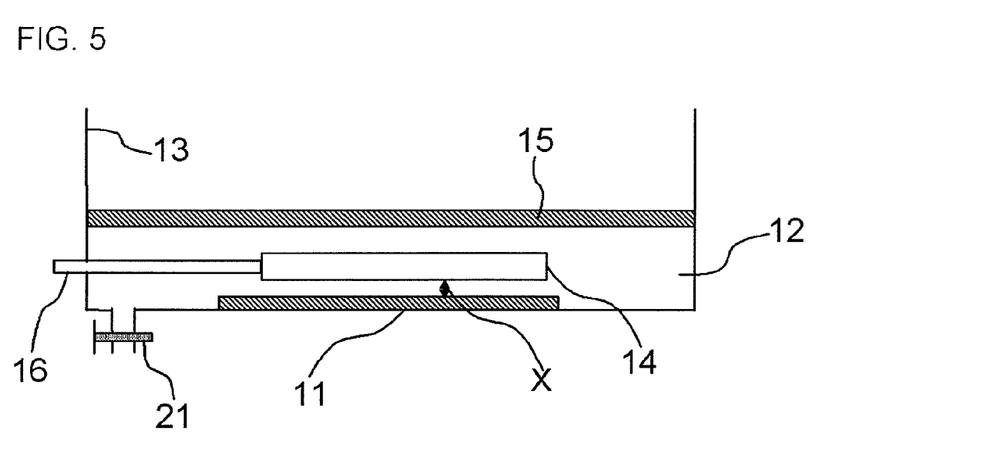
[FIG. 5] It is a schematic diagram, illustrating as measuring device of second embodiment of the present invention.

Second embodiment of the present invention will be described in reference to FIG. 5. In the present embodiment, a discharge section 21 for discharging the liquid contained in the measuring vessel 13 is provided in the measuring vessel 13. Other features are similar to that of the previous embodiment. In the present embodiment, the liquid 12 in the measuring vessel 13 is discharged through the discharge section 21, and new liquid 12 is supplied to the measuring vessel, so that consecutive multiple cycles of the measurements of the component of the gaseous sample can be carried out. In addition to above, when new liquid 12 is supplied in the measuring vessel 13, the feeding duct 16 and the bubble-generating unit 14 may be used, or a supplying section for liquid may be separately provided to supply new liquid 12 in the measuring vessel 13.

It is intended that the present invention is not limited to the above embodiment, and modifications and changes without departing from the spirit of the invention are included in the scope of the invention. For example, while the bubble-generating unit 14 is not in contact with the gas-liquid separator film 15 in the respective embodiments, an arrangement of the bubble-generating unit 14 and the gas-liquid separator film 15 may alternatively be arranged to cause a contact therebetween.

Further, while the gas-liquid separator film 15 is provided to cover the entire surface of the liquid 12 in the respective embodiments, the configuration is not limited thereto, and the liquid 12 may be only partially covered. Further, while the sensor 11 is provided in the bottom of the measuring vessel 13 in the respective embodiments, the configuration is not limited thereto, and the position of the sensor 11 may be arbitrarily selected. For example, the sensor 11 may be fixed to the side section of the measuring vessel 13. In addition to above, the bubble-generating unit 14 may be disposed so that the apertures 141 face the sensor 11. While the apertures 141 are arranged along each side of the bottom surface of the box-shaped vessel in the respective embodiments, the arrangement of the apertures 141 is not limited thereto. The apertures 141 may alternatively be arranged at random. The present application claims a priority based on Japanese patent application No. 2007-86,682 filed Mar. 29, 2007, whole contents of which are incorporated by reference.

Examples

Examples of the present invention will be described below.

Example 1

A measuring device similar as in first embodiment was manufactured. A vinyl chloride sheet having a thickness of 2 mm was processed to manufacture a chassis having an inner dimension of 32 mm (width)×35 mm (height)×32 mm (depth), which serves as a measuring vessel. An adhesive agent for encapsulation was used together with screws in the assembly process. A sensor was designed to have a dimension of 10 mm (width)×10 mm (height)×0.8 mm (thickness), and was fixed to a bottom of the measuring vessel. A vinyl chloride pipe of 5 mm ($\phi$) having a thickness of 1 mm was employed for a feeding duct. A plastic vessel of a rectangular solid having a dimension of 11 mm×11 mm×5 mm was employed for the bubble-generating unit. 10,000 apertures, each having a diameter of 0.05 mm, were provided in a surface opposite to the sensor. The surface of the sensor (detecting surface) was substantially parallel with the surface of the bubble-generating unit opposite to the sensor. A clearance between the bubble-generating unit and the surface of the sensor (the distance between the respective apertures (openings of the respective apertures for discharging bubbles) and the surface of the sensor) was selected to be 0.05 mm. An adhesive agent for encapsulation was employed in the above-mentioned assembly for preventing a leakage of a gas. A volume of the measuring vessel was 28.8 ml.

The manufacture of the sensor was conducted as follows. First of all, a platinum electrode film of 7 mm×4 mm functioning as a detection electrode (working electrode), a platinum electrode film of 7 mm×1 mm functioning as a counter electrode, and a silver/silver chloride electrode film functioning as a reference electrode were provided on a glass substrate (insulating substrate) via a sputter process.

In addition to above, the silver/silver chloride electrode was manufactured by immersing within a ferric chloride solution after silver had been sputtered. Next, alcohol oxidase was immobilized on the surface of the electrodes with albumen and glutaraldehyde. The immobilization of alcohol oxidase was conducted via a spin coating process. Then, wirings were connected to the side surface of the sensor and the bottom surface of the measuring vessel to provide a coupling with the electrochemical measuring device.

A tetrafluoroethylene film (teflon®)) which was processed to have a size of 10 mm×20 mm, was employed for a gas-liquid separator film. A vinyl chloride sheet of 33 mm×32 mm×5 mm(thickness) having apertures of 10 mm×20 mm was employed to fix the tetrafluoroethylene film with screws. Then, the inside of the measuring vessel was filled with a 0.05 mM phosphate buffer (pH 7.6) containing 0.1 mM of sodium chloride.

Example 2

The clearance between the bubble-generating unit and the sensor was set to 0.025 mm. Other features were the same as in Example 1.

Example 3

The clearance between the bubble-generating unit and the sensor was set to 0.046 mm. Other features were the same as in Example 1.

Example 4

The clearance between the bubble-generating unit and the sensor was set to 0.075 mm. Other features were the same as in Example 1.

Comparative Example 1

The clearance between the bubble-generating unit and the sensor was set to 0.02 mm. Other features were the same as in Example 1.

Comparative Example 2

The clearance between the bubble-generating unit and the sensor was set to 0.1 mm. Other features were the same as in Example 1.

Comparative Example 3

The clearance between the bubble-generating unit and the sensor was set to 0.5 mm. Other features were the same as in Example 1.

Evaluations on Examples 1 to 4 and Comparative Examples 1 to 3

A gas containing 10 ppm of alcohol was injected into the measuring device with a pump at a rate of 0.2 ml/second. An electric voltage of 0.7 V was applied to the detection electrode, and time required for obtaining a response electric current until a responding current is obtained was measured. The results are shown in Table 1. Mark "X" represents a result exhibiting a response time of equal to or longer than 10 seconds, mark "O" represents a result exhibiting a response time of not shorter than 7 seconds and shorter than 10 second, and a double circles mark represents a result exhibiting a response time of shorter than 7 seconds.

TABLE 1

| EXAMPLE 1 | ⊚ |
|---|---|
| EXAMPLE 2 | ⊚ |
| EXAMPLE 3 | ⊚ |
| EXAMPLE 4 | ○ |
| COMPARATIVE EXAMPLE 1 | NO RESPONSE |
| COMPARATIVE EXAMPLE 2 | X |
| COMPARATIVE EXAMPLE 3 | X |

It was found that the measuring device exhibits enhanced response speed if the device satisfies the relation of $1/2\ Y \leq X \leq 3/2\ Y$, where X represents the distance of the clearance between the bubble-generating unit and the sensor and Y represents the diameter of the aperture of the bubble-generating unit. In addition to above, it was also found that faster response speed was stably obtained in the case of conducting multiple cycles of measurements with the measuring devices of examples 1 and 3.

Then, measurements were conducted with the measuring devices of Example 1, Comparative Example 1 and Comparative Example 3 in the condition that the device was inclined by 90 degrees to measure the response speeds. While the response speed of of not shorter than 7 seconds and shorter than 10 second was obtained in the device of Example 1, no respond was obtained in the device of Comparative Example 1, and lower response speed was obtained in the device of Comparative Example 3. It was found that faster response speed could be ensured even if the measuring device is inclined in Example 1, and alcohol could quickly be detected. In addition to above, no leakage of the solution was observed in the measuring devices of Example 1, Comparative Example 1 and Comparative Example 3.

Example 5

A measurement vessel similar as employed in Example 1 was produced. The internal capacity of the measurement vessel was 28.5 ml. A trinitrophenol sensor was employed for the sensor manufactured with a carbon paper of a dimension of 7 mm×7 mm×0.5 mm, which was adhered to a surface of a glass substrate of example 1, and then trinitrophenol antibody was immobilized thereto. The process for immobilization involved immersing the glass substrate having the carbon paper adhered thereon in 0.05 mM phosphate buffer solution containing sodium chloride of 0.1 mM (pH 7.6) containing trinitrophenol antibody dissolved therein for 30 minutes, and subsequently immersing thereof in 1% polyvinyl alcohol for 30 minutes. Then, it was also immersed in a saturated tryptophan solution, and then was dried for one hour within a nitrogen atmosphere. A carbon paper commercially available from Toray Industries, Inc. in the name of TGP-H-120 was employed. A monoclonal antibody commercially available from Pharmingen (USA) was employed for trinitrophenol antibody. 0.05 mM phosphate buffer solution containing sodium chloride of 0.1 mM (pH 7.6) was employed for a liquid for filling the measurement vessel. Other features were the same as in Example 1. In addition to above, the diameter of the aperture in the bubble-generating unit was 0.05 mm, similarly as in Example 1, and the clearance between the bubble-generating unit and the sensor was 0.05 mm.

The measuring method and the evaluations will be described.

The measurements were conducted via a square wave voltammetry for sweeping from 0.1 V to 1.2 V under a conditions of an amplitude of 40 mV, 20 Hz, at a step potential of 15 mV. In addition to above, cycles for re-starting the sweeping from 0.1 V after reaching 1.2 V were repeated. A gas of trinitrophenol dissolved in methanol at a concentration of 1 ppm was injected into the measurement vessel with a pump at 0.2 ml/sec. A time required for obtaining a response current in such case was measured. A gaseous methanol was injected into the measurement vessel in similar way for a reference measurement. It was found that a response indicating a current peak was obtained at around 0.8 V after 10 seconds had passed for a gas of trinitrophenol, and therefore trinitrophenol could be detected. On the other hand, no current peak was obtained in the reference experiment.

Example 6

A measurement vessel similar as employed in Example 1 was produced. In the present example, an exhaust port serving as the discharge section for discharging a liquid to the bottom of the measurement vessel was formed. The exhaust port is closed when the measurement vessel is filled with the liquid, and the exhaust port is opened when the liquid is discharged from the measurement vessel. A pH electrode for test tube commercially available from DKK-TOA Corporation under the trade name of ELP-038 was employed for the sensor, and such sensor was fixed to the bottom of the measurement vessel. The pH electrode was coupled to a pH measurement device. Deionized water was employed as the liquid. The internal capacity of the measurement vessel was 28.9 ml.

Other conditions were similar to Example 1.

Figure 6:
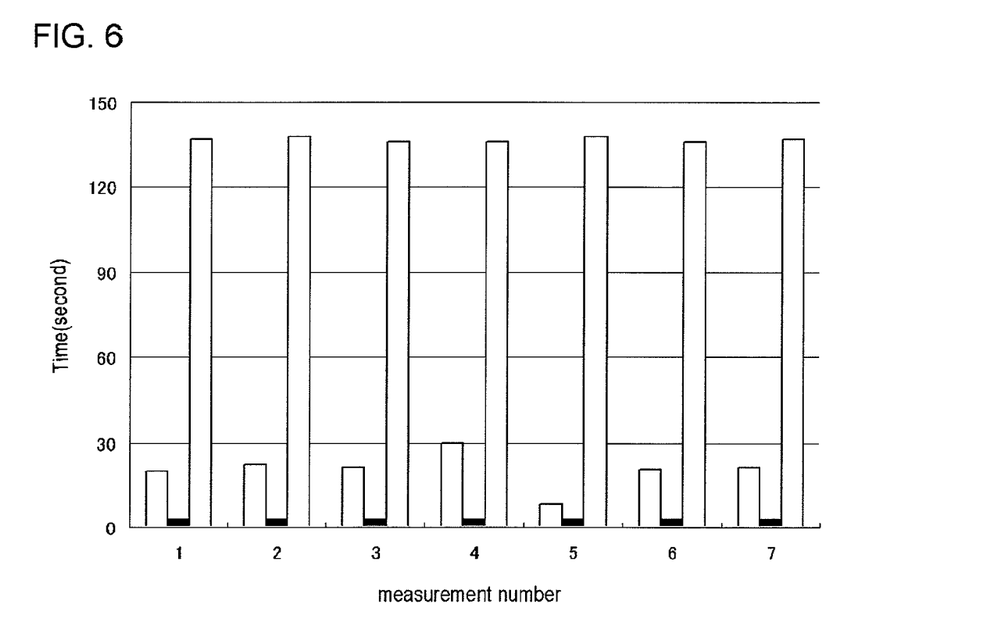
[FIG. 6] It is a graph, showing results of example 6.

A gas of hydrogen chloride of 0.1 M was injected into the measurement vessel at about 0.2 ml/sec with a peristaltic pump SJ-1220 commercially available from ATTO Corporation. A time required for obtaining a response electric current for pH in such case was measured. Further, an injection and a discharging of deionized water were conducted to measure time required for the measurement. The measurements were repeated for seven cycles. In such process, the injection of deionized water was conducted through the feeding duct and the bubble-generating unit. Results are shown in FIG. 6. In each of the measurements shown in FIG. 6, the vertical rectangle in the left side shows time required for filling the measurement vessel with the liquid, the vertical rectangle in the center shows time required for the measurement, and the vertical rectangle in the right side shows time required for discharging the liquid. It was found that a continuous measurement for 160 seconds ±6.0 seconds can be achieved.

The invention claimed is:

1. A measuring device, comprising: a measuring vessel containing a liquid;
   a sensor provided in said measuring vessel for detecting a component of a gaseous sample dissolved in the liquid; and
   a bubble-generating unit being supplied with a gaseous sample and having an aperture for discharging the gaseous sample into the liquid in form of bubbles,
   wherein said aperture faces said sensor and said bubble-generating unit is disposed to have a predetermined clearance with said sensor, and
   wherein a relation of $1/2Y \leq X \leq 3/2Y$ is satisfied,
   where X represents a distance of a clearance between said bubble-generating unit and said sensor and Y represents a diameter of said aperture of said bubble-generating unit.

2. The measuring device as set forth in claim 1, wherein the diameter Y of the aperture of said bubble-generating unit is equivalent to the distance X of the clearance.

3. The measuring device as set forth in claim 1, wherein the diameter Y of the aperture of said bubble-generating unit is equal to or larger than 0.01 mm, and equal to or smaller than 0.1 mm.

4. The measuring device as set forth in claim 1, wherein a discharge section for discharging the liquid is provided to said measuring vessel.

5. The measuring device as set forth in claim 4, wherein the liquid is capable of being supplied to the measuring vessel through said bubble-generating unit.

6. The measuring device as set forth in claim 1, wherein said sensor has a detection electrode, and a protein of biological origin having a catalyst function is fixed to a surface of the detection electrode of said sensor.

7. The measuring device as set forth in claim 6, wherein the protein has at least one of an enzyme and an antibody.

8. The measuring device as set forth in claim 6, wherein said sensor has said detection electrode, a counter electrode and a reference electrode, and wherein said sensor is an amperometric sensor for detecting an electric current obtained from said detection electrode, said detection electrode being applied with an electric potential over said reference electrode.

9. The measuring device as set forth in claim 1, wherein the liquid contains a buffer and an electrolyte.

10. The measuring device as set forth in claim 1, wherein the liquid is supplied to a region comparted by said measuring vessel and a gas-liquid separator membrane, and wherein said gas-liquid separator membrane contains tetrafluoroethylene as a major constituent.

11. The measuring device as set forth in claim 1, wherein said bubble-generating unit has a plurality of said apertures.

12. The measuring device as set forth in claim 1, wherein the distance X of a clearance between said bubble-generating unit and said sensor is presented as a distance between the closest one of said apertures formed in said bubble-generating unit and said sensor, said closest one of said apertures being leastwise closest to said sensor.

13. The measuring device as set forth in claim 12, wherein a plurality of said apertures are formed in said bubble-generating unit, and wherein the distances X of the clearances between the respective all of said apertures and said sensor satisfy the relation of: $1/2Y<X<3/2Y$.

* * * * *